US008853380B2

(12) United States Patent
Salunkhe et al.

(10) Patent No.: US 8,853,380 B2
(45) Date of Patent: Oct. 7, 2014

(54) MODIFIED SAK GENE FOR THE PRODUCTION OF RECOMBINANT PROTEINS

(75) Inventors: Shardul Salunkhe, Maharashtra (IN); Bhaskarjyoti Prasad, Maharashtra (IN); Praveen Muneshwar, Maharashtra (IN); Anjali Apte Deshpande, Maharashtra (IN); Sriram Padmanabhan, Maharashtra (IN)

(73) Assignee: Lupin Limited, Mumbai, Maharashtra (IN)

( * ) Notice: Subject to any disclaimer, the term of this patent is extended or adjusted under 35 U.S.C. 154(b) by 0 days.

(21) Appl. No.: 13/702,028

(22) PCT Filed: Jun. 3, 2011

(86) PCT No.: PCT/IB2011/001210
§ 371 (c)(1),
(2), (4) Date: Dec. 4, 2012

(87) PCT Pub. No.: WO2011/151714
PCT Pub. Date: Dec. 8, 2011

(65) Prior Publication Data
US 2013/0122542 A1    May 16, 2013

(30) Foreign Application Priority Data
Jun. 4, 2010 (IN) .............................. 607/KOL/2010

(51) Int. Cl.
| *C07H 21/04* | (2006.01) |
| *C12N 9/00* | (2006.01) |
| *C12P 21/06* | (2006.01) |
| *C07K 14/555* | (2006.01) |
| *C07K 14/535* | (2006.01) |
| *C07K 14/54* | (2006.01) |
| *C07K 14/49* | (2006.01) |
| *C07K 14/55* | (2006.01) |
| *C12N 9/96* | (2006.01) |
| *C07K 14/635* | (2006.01) |
| *C12N 9/72* | (2006.01) |
| *C07K 14/31* | (2006.01) |
| *C07K 14/485* | (2006.01) |

(52) U.S. Cl.
CPC .......... *C12P 21/06* (2013.01); *C12Y 304/21069* (2013.01); *C07K 14/555* (2013.01); *C07K 2319/35* (2013.01); *C07K 14/535* (2013.01); *C07K 14/5412* (2013.01); *C07K 14/49* (2013.01); *C07K 14/5403* (2013.01); *C07K 14/5406* (2013.01); *C07K 14/5431* (2013.01); *C07K 14/55* (2013.01); *C12N 9/96* (2013.01); *C07K 14/5409* (2013.01); *C07K 14/635* (2013.01); *C12N 9/6459* (2013.01); *C07K 2319/50* (2013.01); *C07K 14/31* (2013.01); *C07K 14/485* (2013.01)
USPC .......................... 536/23.4; 435/183; 435/68.1

(58) Field of Classification Search
CPC ........ C12P 21/02; C12P 13/00; C12P 13/005; C12P 13/04; C12P 13/22; C12P 19/26; C12P 21/00; C12P 17/04; C12P 21/06; C12N 15/67; C12N 9/93; C12N 9/6435; C12N 9/96; C12N 15/1044; C12N 15/11; C12N 2510/02; C12N 9/14; C12N 9/6459; C12N 9/99; C12N 15/102; C12N 15/1034; C12N 15/1058; C12N 15/113; C12N 15/62; C12N 15/625; C12N 15/70; C12N 15/85; C12N 2799/026; C12N 2799/027; C12N 5/0636; C12N 5/0646; C12N 5/0695; C12N 9/003; C12N 9/0051; C12N 9/1007; C12N 9/1241; C12N 9/1247; C12N 9/2402; C12N 9/2465; C12N 9/48; C12N 9/52; C12N 9/82
See application file for complete search history.

(56) References Cited

FOREIGN PATENT DOCUMENTS

| EP | 1 598 364 | 11/2005 |
| IN | 1813/KOL/2002 | 10/2008 |

OTHER PUBLICATIONS

Salunkhe et al. Expression and purification of SAK-fused human interferon alpha in *Escherichia coli*. Journal of Microbial and biochemical technology. 2009; 1(1):5-10.*
Apte-Deshpnade et al., "High-level expression of non-glycosylated and active staphylokinase from *Pichia pastoris*", *Biotechnol Lett*, vol. 31, 2009, pp. 811-817.
Gardella et al., "Expression of Human Parathyroid Hormone-(1-84) in *Escherichia coli* as a Factor X-cleavable Fusion Protein", *The Journal of Biological Chemistry*, vol. 265, No. 26, 1990, pp. 15854-15859.
International Search Report and Written Opinion from International Application No. PCT/IB2011/001210 mailed Sep. 21, 2011.
Jackson et al., "Complete Amino Acid Sequence of Streptokinase and Its Homology with Serine Proteases", *Biochemistry*, vol. 21, 1982, pp. 6620-6621.
Liu et al., "Large scale preparation of recombinant human parathyroid hormone 1-84 from *Escherichia coli*", *Protein Expression and Purification*, vol. 54, 2007, pp. 212-219.
Mandi et al., "High yielding recombinant Staphylokinase in bacterial expression system-cloning, expression, purification and activity studies", *Protein Expression and Purification*, vol. 64, 2009, pp. 69-75.
Prasad et al., "Novel self-cleavage activity of Staphylokinase fusion proteins: An interesting finding and its possible applications", *Protein Expression and Purification*, vol. 69, 2010, pp. 191-197.

(Continued)

*Primary Examiner* — Vanessa L. Ford
*Assistant Examiner* — Sandra Dillahunt
(74) *Attorney, Agent, or Firm* — Merchant & Gould P.C.

(57) ABSTRACT

The present invention relates to modified SAK gene having amino acid SEQ ID 2. The present invention further relates to process for cloning and expressing modified SAK gene fusion protein which imparts improved stability to the heterologous protein of interest. Further the invention relates to process of purification of recombinant heterologous proteins from bacterial inclusion bodies using modified SAK.

7 Claims, 2 Drawing Sheets

(56) References Cited

OTHER PUBLICATIONS

"Protocol 8: Purification of Expressed Proteins from Inclusion Bodies", *Molcular Cloning: A Laboratory Manual*, 3$^{rd}$ ed., 2002, pp. 15.49-15.54.

Rabijns et al., "Three-dimensional structure of staphylokinase, a plasminogen activator with therapeutic potential", *Nature Structural Biology*, vol. 4, No. 5, 1997, pp. 357-360.

Ren et al., "Novel preparation protocol for the expression and purification of recombinant staphylokinase", *Biotechnol. Appl. Biochem.*, vol. 51, 2008, pp. 9-13.

Sakharov et al., "Interactions between Staphylokinase, Plasmin(ogen), and Fibrin", *The Journal of Biological Chemistry*, vol. 271, No. 44, 1996, pp. 27912-27918.

Salunkhe et al., "Expression and Purification of SAK-fused Human Interferon Alpha in *Escherichia coli*", *Journal of Microbial & Biochemical Technology*, vol. 1, Issue 1, 2009, pp. 5-10.

Schlott et al., "NH$_2$-terminal Structural Motifs in Staphylokinase Required for Plasminogen Activation", *The Journal of Biological Chemistry*, vol. 273, No. 35, 1998, pp. 22346-22350.

Scopes, Robert K., *Protein Purification: Principles and Practice*, Third edition, Chapters 1, 4, 5, 6, 7 and 8, *Springer-Verlag, New York, Inc.*, New York, 1994, Second reprint 2005.

Shatzman et al., "Expression, Identification, and Characterization of Recombinant Gene Products in *Escherichia coli*", Berger and Kimmel, *Guide to Molecular Cloning Techniques, Methods in Enzymology*, vol. 152, 1987, pp. 661-673.

Struhl, Kevin, "Enzymatic Manipulation of DNA and RNA", Chapter 3, *Current Protocols in Molecular Biology, Supplement 58*, 2002, pp. 3.0.1-3.0.2.

\* cited by examiner

MODIFIED SAK GENE FOR THE PRODUCTION OF RECOMBINANT PROTEINS

This application is a National Stage Application of PCT/IB2011/001210, filed 3 Jun. 2011, which claims benefit of Serial No. 607/KOL/2010, filed 4 Jun. 2010 in India and which application(s) are incorporated herein by reference. To the extent appropriate, a claim of priority is made to each of the above disclosed applications.

FIELD OF THE INVENTION

The present invention relates to a cloning and expressing modified SAK gene fusion protein which imparts improved stability to the heterologous protein of interest. Further the invention relates to process of purification of recombinant heterologous proteins from bacterial inclusion bodies using modified Staphylokinase protein carrying internal EK site.

BACKGROUND OF THE INVENTION

Fusion proteins are proteins created through the joining of two or more genes which originally code for separate proteins. Translation of this fusion gene results in a single polypeptide with functional properties derived from each of the original proteins. Recombinant fusion proteins are created artificially by recombinant DNA technology for use in biological research or therapeutics.

Several techniques are available for producing fusion proteins which retain the desirable characteristics of thermostability, solubility and a high level of expression.

The most commonly used method for producing fusion proteins is use of fusion tags. Examples of popular fusion tags include, Histidine-tag, glutathione-s-transferase (GST), Maltose binding protein, NusA, thioredoxin (TRX), polyhistidine (HIS), small ubiquitin-like modifier (SUMO) and ubiquitin (Ub).

One of the strategies provides a method to express protein of interest as a staphylokinase (SAK) fusion. Since one can easily assay SAK activity using the simple chromogenic assay, one could adopt the SAK assay as a measure of successful refolding of the SAK fusion protein. SAK is a 136 amino acid long bacteriophage encoded protein of 15.5-kDa size and is devoid of disulphide linkages. SAK is presently undergoing clinical trials for blood clot-lysis in the treatment of thrombovascular disorders due to its ability to convert plasminogen, (an inactive proenzyme of the fibrinolytic system) into plasmin, which is a protease. SAK has gained importance as a potential therapeutic thrombolytic protein and is an extracellular protein produced by *Staphylococcus aureus* strains. It is also produced by *S. lyicus, S. simulans, S. seweri* and *S. xylosus*. Schlott et al 273(35): 22346-50, 1998, have disclosed that SAK is not an enzyme, but rather a cofactor; it forms a 1:1 stoichiometric complex with plasmin(ogen) that converts other plasminogen molecules to plasmin, a potent enzyme that degrades proteins of the extracellular matrix. The high affinity of the SAK-plasminogen complex for fibrin makes it a promising thrombolytic agent.

Jackson and Tang, Biochemistry, 21(26): 6620-5, 1982 have reported that SAK has been shown to be homologous to serine proteases although it does not have any protease activity of its own. Sakharav et al J. Biol. Chem. 271: 27912-27918, 1996, have reported that SAK structurally resembles plasminogen activators, has plasminogen-binding site and serine protease domain but does not show protease activity.

IN/1813/KOL/2008 describes that SAK has proteolytic activity, Salunkhe et al 1(1): 5-10, 2009, have reported that the expression levels of SAK-IFN were found to be two folds higher than that observed with untagged IFN under similar experimental conditions. It has been observed that a full length SAK (FL-SAK) when expressed results into 2 fragments as mature SAK and signal peptide. It was found that when FL-SAK was expressed in BL21-A1 cells resulted into 2 fragments as mature SAK and signal protein. This proves that SAK has autoproteolytic property when used as C-terminus fusion. Thus, SAK can be used as a proteolytic tool by exploring its autoproteolytic activity. One of the problems associated with use of SAK for the expression of protein of interest is that the protein of interest is also degraded after release of SAK protein from fusion protein.

SUMMARY OF THE INVENTION

In an aspect the invention is related to fusion protein DNA comprising a first DNA encoding a modified SAK protein having the nucleotide sequence of SEQ ID No. 1 and a second DNA fused in the frame encoding the heterologous protein of interest.

In another aspect the invention is related to fusion protein DNA comprising a first DNA encoding a modified SAK protein having the amino acid of SEQ ID No. 2 and a second DNA fused in the frame encoding the heterologous protein of interest.

In another aspect the invention relates to a process for the preparation of heterologous protein in *E. coli* comprising the steps of:

a) preparing a fusion DNA comprising a first DNA encoding modified SAK protein and a second DNA fused in the frame encoding the heterologous protein of interest, b) cloning of the fusion DNA of step a into an expression vector, c) expressing the fusion protein in *E. coli* cells, d) optionally refolding and purifying the fusion protein;

e) enterokinase cleavage of fusion protein, and f) isolating and purifying the protein of interest to obtain pure heterologous protein.

In yet another aspect the invention provides method for purification of modified SAK fusion protein wherein, the fusion protein is expressed as inclusion bodies in *E. coli* comprising the steps of:

a) solubilizing the inclusion bodies, b) refolding the solubilizing inclusion bodies, c) enterokinase digestion of modified SAK fusion protein, and d) isolating and purifying the protein of interest by one or more of chromatographic techniques.

In an embodiment of the invention the protein may be refolded before or after enterokinase digestion.

In another embodiment the fusion protein or the protein of interest can be purified by purification methods comprising Ion exchange chromatography, affinity chromatography hydrophobic interaction chromatography, reverse phase chromatography and gel filtration chromatography The details of one or more embodiments of the inventions are set forth in the description below. Other features, objects and advantages of the inventions will be apparent from the description.

DESCRIPTION OF SEQUENCE ID

```
SEQ ID NO. 1: Nucleic acid sequence of modified SAK
Modified SAK
catatgtcaa gttcattcga caaaggaaaa tataaaaaag gcgatgacgc gagttatttt gaaccaacag gcccgtattt gatggtaaat gtgactggag ttgatggtaa aggaaatgag ttgctatccc ctcattatgt cgagtttcct attaaacctg ggactacact tacaaaagaa aaaattgaat acgatgatga tgataaagaa tgggcattag atgcgacagc atataaagag tttagagtag ttgaattaga tccaagcgca aagatcgaag tcacttatta tgataagaat aagaaaaaag aagaaacgaa gtctttccct ataacagaaa aaggttttgt tgtcccagat ttatcagagc atattaaaaa ccctggattc aacttaatta caaaggttgt tatagaaaag aaagatgatg atgataaata a SEQ ID NO. 2: Amino acid sequence of modified SAK
Modified SAK
Msssfdkgky kkgddasyfe ptgpylmvnv tgvdgkgnel lsphyvefpi kpgttltkek ieylqddddk yvewaldata ykefrvveld psakievtyy dknkkkeetk sfpitekgfv vpdlsehikn pgfnlitkvv iekkgsdddd k SEQ ID NO. 3: Nucleic acid sequence of modified SAK-PTH fusion protein
Modified SAK-PTH fusion protein
catatgtcaa gttcattcga caaaggaaaa tataaaaaag gcgatgacgc gagttatttt gaaccaacag gcccgtattt gatggtaaat gtgactggag ttgatggtaa aggaaatgag ttgctatccc ctcattatgtc gagtttccta ttaaacctgg gactacactt acaaaagaaa aaattgaata cctgcaggat gatgatgata aatacgtaga atgggcatta gatgcgacag catataaaga gtttagagta gttgaattag atccaagcgc aaagatcgaa gtcacttatt atgataagaa taagaaaaaa gaagaaacga agtctttccc tataacagaa aaaggttttg ttgtcccaga tttatcagag catattaaaa accctggatt caacttaatt acaaaggttg ttatagaaaa gaaaggatcc gatgatgatg ataaatctgt gtccgagatt cagttaatgc ataaccttgg caaacatttg aactccatgg agcgtgtaga atggctgcgt aagaagttgc aggatgtgca caatttttaa SEQ ID NO. 4: Amino acid sequence of modified SAK-PTH fusion protein
Modified SAK-PTH fusion protein
msssfdkgky kkgddasyfe ptgpylmvnv tgvdgkgnel lsphyvefpi kpgttltkek ieylqddddk yvewaldata ykefrvveld psakievtyy dknkkkeetk sfpitekgfv vpdlsehikn pgfnlitkvv iekkgsdddd ksyseiqlmhn lgkhlnsmer vewlrkklqd vhnf SEQ ID NO. 5: Nucleic acid sequence of modified SAK-IL-11 fusion protein
Modified SAK-IL-11 fusion protein
catatgtcaa gttcattcga caaaggaaaa tataaaaaag gcgatgacgc gagttatttt gaaccaacag gcccgtattt gatggtaaat gtgactggag ttgatggtaa aggaaatgag ttgctatccc ctcattatgt cgagtttcct attaaacctg ggactacact tacaaaagaa aaaattgaat acctgcagga tgatgatgat aaatacgtag aatgggcatt agatgcgaca gcatataaag agtttagagt agttgaatta gatccaagcg caaagatcga agtcacttat tatgataaga ataagaaaaa agaagaaacg aagtctttcc ctataacaga aaaaggtttt gttgtcccag atttatcaga gcatattaaa aaccctggat tcaacttaat tacaaaggtt gttatagaaa agaaaggatc cgatgatgat gataaagggc caccacctgg cccccctcga gtttccccag accctcgggcc gagctggaca gcaccgtgct cctgacccgc tctctcctgg cggacacgcg gcagctggct gcacagctga gggacaaatt cccagctgac ggggaccaca acctggattc cctgcccacc ctggccatga gtgcgggggc actgggagct ctacagctcc caggtgtgct gacaaggctg cgagcggacc tactgtccta cctgcggcac gtgcagtggc tgcgccgggc aggtggctct tccctgaaga ccctggagcc cgagctgggc accctgcagg cccgactgga ccggctgctg cgccggctgc agctcctgat gtcccgcctg gccctgcccc agccaccccc ggacccgccg gcgcccccgc tggcgccccc ctcctcagcc tggggggggca tcagggccgc ccacgccatc ctgggggggc tgcacctgac acttgactgg gccgtgaggg gactgctgct gctgaagact cggctgtga
```

-continued

```
SEQ ID NO. 6: Amino acid sequence of modified SAK-IL-11 fusion protein
Modified SAK-IL-11 fusion protein
MSSSFDKGKY KKGDDASYFE PTGPYLMVNV TGVDGKGNEL LSPHYVEFPI

KPGTTLTKEK IEYLQDDDDK YVEWALDATA YKEFRVVELD PSAKIEVTYY

DKNKKKEETK SFPITEKGFV VPDLSEHIKN PGFNLITKVV IEKKGSDDDD

KGPPPGPPRV SPDPRAELDS TVLLTRSLLA DTRQLAAQLR DKFPADGDHN

LDSLPTLAMS AGALGALQLP GVLTRLRADL LSYLRHVQWL RRAGGSSLKT

LEPELGTLQA RLDRLLRRLQ LLMSRLALPQ PPPDPPAPPL APPSSAWGGI

RAAHAILGGL HLTLDWAVRG LLLLKTRL
```

DETAILED DESCRIPTION OF THE INVENTION

According to the present invention, the DNA sequence encoding a heterologous peptide or protein selected for expression in a recombinant system is fused to a modified SAK DNA sequence having SEQ ID No. 1 for expression in the host cell. A modified SAK DNA sequence having SEQ ID NO. 1 is defined herein as a DNA sequence carrying an enterokinase site in the SnaBI site inside the SAK gene. In modified SAK the autoproteolytic activity of SAK protein is blocked due to insertion of EK site at 65$^{th}$ aa position (65$^{th}$ and 69$^{th}$ aa of SAK are reported to be important for complex formation with plasminogen and induction of active site exposure (Rabijns et al. Nature structural biology, 4(5): 357-360, 1997).

In an embodiment the modified SAK DNA sequence of the invention may be used to express various proteins of interest as fusion protein of modified SAK protein. A wide variety of heterologous genes or gene fragments may be used for example but not limited to hormones, cytokines, growth or inhibitory factors, enzymes, modified or wholly synthetic proteins or peptides for producing corresponding protein of interest.

The term “protein of interest” as used herein refers to any protein or peptide, the production of which is desirable. In one embodiment, the protein or peptide is biologically active. Examples of proteins of interest include, but are not limited to, interleukins i.e. IL-11, IL-2, IL-3, IL-4, IL-5, IL-6, IL-7, IL-8, IL-10, IL-13, IL-15, IL-18, reteplase, parathyroid hormone(1-34), parathyroid hormone(1-84), thrombopoietin, epidermal growth factor, basic fibroblast growth factor, granulocyte-macrophage colony stimulating factor, human growth hormone, granulocyte colony stimulating factor, macrophage colony stimulating factor, platelet-derived growth factor, interferons including IFN-alpha, IFN-beta, IFN-gamma, cleavage enzymes such as Factor Xa, thrombin, OmpT and others similar small peptides.

In another embodiment, the protein of interest is human parathyroid hormone PTH (1-34) and PTH (1-84). Parathyroid hormone is an endocrine hormone synthesized and secreted by parathyroid gland and regulates calcium and phosphate homeostasis by acting on specific cells in bone and kidney. Recombinant hPTH is a potent anabolic agent used in the treatment of osteoporosis. Endogenous PTH is the primary regulator of calcium and phosphate metabolism in bone and kidney.

Teriparatide (PTH(1-34)) is a truncated portion of full length parathyroid hormone having amino acid sequence 1 through 34 of the complete molecule comprising 84 amino acids. It has been approved for the treatment of osteoporosis. Daily injections of PTH(1-34) help to stimulate new bone formation leading to increased bone mineral density. Fusion proteins of PTH have been reported with proteins like Streptavidin, Human growth hormone (Gardella et al J Biol. Chem. 265(26):15854-9, 1990), His-thioredoxin (Liu et al Protein Express Purification 54:212-219, 2007), in *E. coli* expression system.

In another embodiment, the protein of interest is interleukins. In a preferred embodiment, the protein of interest is IL-11. IL-11 is a 19 kDa polypeptide consisting of 178 amino acids, which does not contain potential glycosylation residues, disulphide bonds or other post-translational modifications. It binds to a multimeric receptor complex which contains an IL-11 specific α-receptor subunit and a promiscuous β subunit (gp130). IL11 has been demonstrated to improve platelet recovery after chemotherapy-induced thrombocytopenia, induces acute phase proteins, modulates antigen-antibody responses, participates in the regulation of bone cell proliferation and differentiation and could be use as a therapeutic for osteoporosis. Examples of popular fusion tags for preparation of IL11 fusion protein includes glutathione-s-transferase (GST), Maltose binding protein, NusA, thioredoxin (TRX), polyhistidine (HIS), small ubiquitin-like modifier (SUMO) and ubiquitin (Ub). EP1598364A1 discloses novel polynucleotide encoding fusion interleukin (IL)-11 receptor and IL-11 polypeptide.

In another embodiment there is provided a method of preparing heterologous fusion protein which further refers to polypeptides and proteins which comprise a protein of interest and a modified SAK protein. Modified SAK protein carries an enterokinase site inside the SAK gene. Modified SAK fusion protein is cleaved with enterokinase at two sites one is between SAK and protein of interest and other is inside the SAK protein. After cleavage of the modified SAK protein it loses its proteolytic activiy and also staphylokinase activity and could not degrade the protein of interest further.

In an embodiment different expression vectors may be used for example plasmid, pET or pBAD, pTOPO or any other expression vector. In a preferred embodiment of the invention the vector is pET-21a. Though pET-21a contains an inherent ampicillin (antibiotic) marker for selection of transformants, other antibiotic markers like chloramphenicol acyl transferase (CAT), Kanamycin (APH, phosphotransferases), tetracycline resistance gene etc. may be used as antibiotic markers. These markers may be cloned either under a constitutive promoter or under their own respective promoters at suitable restriction sites of the vector. Genes of interest are cloned in pET plasmids under control of strong bacteriophage T7 promoter carrying transcription and translation signals is induced by an inducer which induces expression of T7 RNA polymerase from the host cell which in turn stimulates expression of protein of interest. T7 RNA polymerase is so selective and active that almost all of the cell's resources are utilized for gene expression. Vectors carrying genes of interest are initially propagated in hosts that do not carry T7 RNA polymerase gene in their genomes, so they are virtually "off" and cannot cause plasmid instability due to the production of proteins potentially toxic to the host cell. Once established, plasmids are transferred into expression hosts containing a chromosomal copy of the T7 RNA polymerase gene under lacUV5 control.

The inducible promoters used in the fermentation may be T7 polymerase, uspA or araBAD or any other promoter present in expression vectors.

The inducer used with the expression construct may be selected from IPTG, lactose, arabinose or maltose. The use of inducer may be known to person skilled in the art.

Various strains of E. coli may be used for the process of the present invention for example cells which are protease deficient strains such as BL21, ER2566 and the protease expressing strains of K12 derivatives such as HB101, JM109, LE392, C600, TOP10, DH5 alpha and the like.

In preferred embodiment of the invention BL21 (DE3) codon plus competent cells are made for high level protein expression and easy induction in T7 expression systems. These cells contain a CO1E1 compatible pACYA based plasmid containing extra copies of the argU, ileY, proL and leuW tRNA genes thus will provide enough tRNA pool for expression of proteins containing these rare codons for arginine, isoleucine, proline and leucine amino acids. These cells exhibit antibiotic resistance for chloramphenicol.

In an embodiment the modified cells cloned with SAK-Protein of interest were selected for fermentation process. The fermentation was carried out in the batch mode using complex medium comprised of salts like sodium phosphate and potassium phosphate. Inducer used was IPTG and fermentation batch time was ~7 to 8 hours. Growth inhibition was not observed inspite of inducer addition, this helped to achieve higher biomass along with expression of protein of interest. This resulted in higher yield of the process A frequently occurring problem in production of recombinant proteins in Prokaryotic cells is the formation of hardly soluble intracellular aggregates of denatured forms of protein expressed called as inclusion bodies, which partially have a secondary structure and can be found in the cytoplasm of the bacterial cells. The formation of said inclusion bodies leads to the necessity of solubilizing and renaturing the proteins subsequent to the isolation of the inclusion bodies by means of centrifugation at moderate speed with the aid of suitable means in order to maintain their active configuration. Herein, the competitive reaction between a transfer of the denatured protein into the right folding intermediate and an aggregation of several protein molecules is an essential factor limiting the yield of renatured protein.

In further embodiment the invention further provides a process for production of pure protein of interest from the inclusion bodies. For obtaining the pure proteins from the inclusion bodies one skilled in the art can follow the procedures described in the literature. Typically the process for the production of pure protein of interest from the inclusion bodies includes solubilizing the inclusion bodies of proteins; refolding the said solubilized proteins; purifying the refolded proteins; and isolating pure proteins wherein, the purification step may be performed more than once before and after the refolding step.

In yet another embodiment the process for production of pure protein of interest from the inclusion bodies includes solubilizing the inclusion bodies of proteins; refolding the said solubilized proteins; enterokinase digestion of the refolded protein, purifying the digested proteins; and isolating pure proteins wherein the steps can be performed in any order.

There are various methods reported in the literature, one skilled in the art can follow one or more methods to obtain protein of interest. Such techniques have been extensively described in Berger and Kimmel, Guide to Molecular Cloning Techniques, Methods in Enzymology, Volume 152, Academic Press, San Diego, Calif. (1987); Molecular Cloning: A Laboratory Manual, 2d ed., Sambrook, J., Fritsch, E. F., and Maniatis, T. (1989); Current Protocols in Molecular Biology, John Wiley & Sons, all Viols., 1989, and periodic updates thereof; New Protein Techniques Methods in Molecular Biology, Walker, J. M., ed., Humana Press, Clifton, N.J., 1988; and Protein Purification: Principles and Practice, 3rd. Ed., Scopes, R. K., Springer-Verlag, New York, N.Y., 1987, the above are incorporated herein by references in its entirety. In general, techniques including, but not limited to, ammonium sulfate precipitation, centrifugation, ion exchange, reverse-phase chromatography, affinity chromatography, hydrophobic interaction chromatography may be used to further purify the protein.

In yet another embodiment, the invention presents a method for purification of fusion protein expressed as inclusion bodies. The inclusion bodies are solubilized, filtered and refolded by fast dilution drop wise into refolding buffer followed by diafiltration.

The solubilization buffer is selected from buffer A (100 mM Tris, 6 M GuHCl, pH 8.0), buffer B (6M GuHCl, 20 mM Tris-Cl, pH 8.0). The solubilization step comprises centrifugation or continuous stirring to ensure complete solubilization of the inclusion bodies in the solubilization buffer. The refolding buffer comprises one or more buffers selected from buffer A (20 mM Tris, 0.5 M Arginine, 5% Sorbitol, 2 mM EDTA, pH 8.0), buffer B (20 mM Tris, 4 M urea, pH 8.0) and buffer C (20 mM Tris-Cl, pH 8.0, 0.5M Arginine, 5% Sorbitol and 1 mM EDTA). The solubilization and refolding steps may optionally be followed by diafiltration.

In another embodiment of the invention, the refolded fusion protein is digested with enterokinase (Novagen bovine enterokinase) at RT in 1 mM $CaCl_2$ to release protein of interest. The enterokinase digestion of the fusion protein is followed by centrifugation and the supernatant obtained after centrifugation is further used for purification of the protein of interest.

The protein of interest may be further purified using one or more purification steps. The purification steps include affinity chromatography, metal affinity chromatography, hydrophobic interaction chromatography, ion exchange chromatography, Size exclusion chromatography and others. The sequence of the chromatography may be in any order depending on the protein of interest and nature of impurities.

The purity of the purified protein is 99% as determined by RP-HPLC. The purified proteins can further be used for making pharmaceutical compositions.

The invention is further illustrated by the following examples which are provided merely to be exemplary of the invention and do not limit the scope of the invention. Certain modifications and equivalents will be apparent to those skilled in the art and are intended to be included within the scope of the invention.

Example 1

Construction of pET21a-Staphylokinase (SAK) Vector

In-house pET21a-SAK vector was constructed using synthetic staphylokinase (SAK) gene as a template. SAK gene was amplified using gene specific primers and digested with NdeI-BamHI enzymes and ligated to pET21a vector at the same site.

Also, a pET-modified SAK-gene of interest clone was constructed, after construction of pET-SAK-gene of interest clone. Site directed mutagenesis was performed to insert SnaBI site into the native SAK gene which is cloned as NdeI/BamHI in pET21a vector. An additional enterokinase site was then introduced into the SnaBI site by an additional cloning step. Thus the final pET21a-modified SAK clone contains two enterokinase sites.

The gene of interest for the desired protein was synthesized with suitable restriction sites at both the 5' and the 3' end as a synthetic DNA fragment and used as a template for further cloning experiments. This gene of interest was PCR amplified, purified and digested with BamHI/HindIII and cloned in pET-SAK and pET-modified SAK vectors at BamHI/HindIII sites and expressed in E. coli BL21(DE3) Codon plus cells as a fusion protein upon induction in 1 mM IPTG.

The basic transformation for the expression studies is by selective induction using a non-metabolisable inducer. Briefly, the mixture of a recombinant expression construct namely pET21a-SAK-gene of interest and pET21a-modified SAK-gene of interest and BL21 (DE3) Codon plus competent cells were incubated on ice for 30 min individually, followed by heat shock at 42° C. for 2 min. Post heat shock the cells were placed on ice for 2 min and 800 µl of Luria Bertanni broth (LB) medium was added and incubated additionally for 1 hr at 37° C. After 1 hr, the culture (suitable volume) is plated on a LB agar plate containing ampicillin and chloramphenicol antibiotic at 100 µg/ml and 34 µg/ml final concentrations of both the antibiotics respectively. The plates after incubation at 37° C. for 16-18 hr were used for further selection of transformants. The recombinant clones from both the vectors carrying the plasmid with the protein of interest gene were chosen for expression studies.

Example 2

Expression of SAK-Protein of Interest Fusion Protein

Expression of the gene of interest is achieved in shake flask studies. Briefly, 50 ml of LB with amp and chloramphenicol was added and the BL21 (DE3) codon plus cells carrying either pET21a-SAK-gene of interest and pET21a-modified SAK-gene of interest constructs were grown at 37° C. till the absorbance of 1.0 at 600 nm. The cultures were induced with 1 mM IPTG for 4 hours and the samples were analyzed on a 15% denaturing polyacrylamide gels (SDS-PAGE) with suitable negative control (pET21 alone) and suitable protein molecular weight marker. Finally, the gels were visualized with CBB R-250 staining. After EK digestion of SAK-Protein of interest fusion at various time points, the protein of interest was not visible on a suitable Tricine gel. This was thought to be due to the proteolytic activity of released SAK on the released protein of interest after the EK digestion. When the modified SAK-gene of interest fusion was digested with EK, the cleavage occurred at 2 sites one between modified-SAK and the protein of interest and other was inside the SAK protein. Due to the cleavage of SAK protein, the SAK as a SAK* lost its proteolytic activity and also the staphylokinase activity and hence could not degrade the protein of interest further. To test this hypothesis, SAK activity was tested for both the fusion proteins.

Example 3

Chromogenic Assay of SAK

SAK activity was quantified using plasminogen coupled chromogenic assay as described by Deshpanade et. al. Biotechnol. Lett 31: 811-817, 2009. Briefly, 25 mU of human plasminogen, chromogenic substrate D-Val-Leu-Lys 4-nitroanilide dihydrochloride (Sigma) and samples containing SAK were incubated in 100 µl reaction volume in 96-well flat-bottom plates (Nunc) at 25° C. for 20 min. Amount of p-nitroaniline (pNA) released was monitored at 405 nm by plate reader (Multiskan Spectrum, Thermo, USA). One unit (1 U) of SAK is the amount of the enzyme needed to form 1 U of plasmin from plasminogen. Units of plasmin formed were estimated from the amount of chromogen (pNA) formed using a standard curve of pure pNA.

Figure 1:
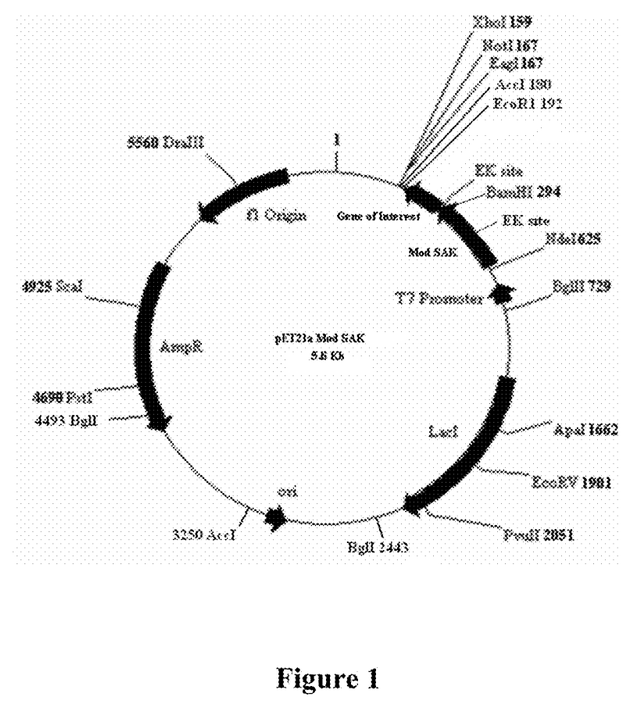
FIG. 1: Construction of pET21a-SAK-Protein of interest gene expression vector
Figure 2:
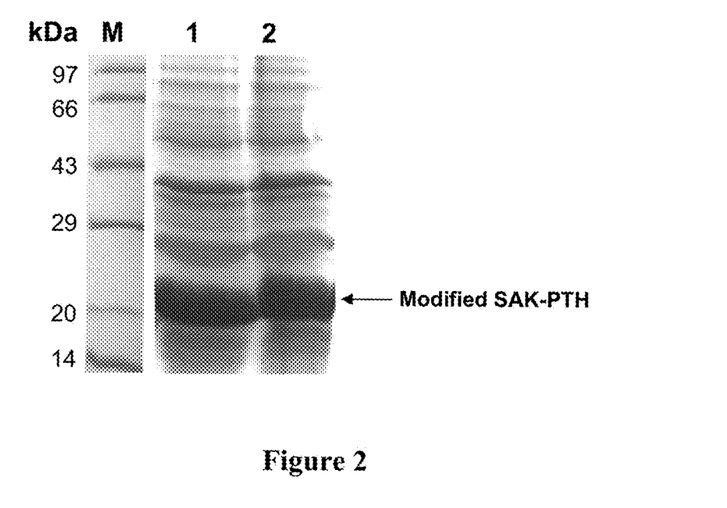
FIG. 2: Modified SAK-PTH expression in inclusion bodies
Figure 3:
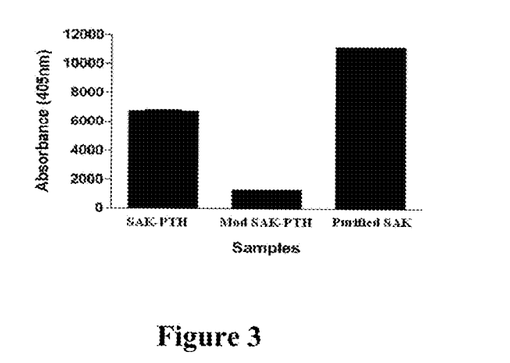
FIG. 3: Staphylokinase activity in SAK-PTH and modified SAK-PTH fusions

FIG. 3 depicts that SAK-protein of interest fusion has active staphylokinase whereas the activity is lost in modified SAK-protein of interest fusion.

Modified SAK-protein of interest fusion clone was therefore used in further fermentation process.

Example 4

Modified SAK-Protein of Interest Fermentation Process

Modified SAK-protein of interest fermentation was carried out in the batch mode using complex medium comprised of salts like sodium phosphate and potassium phosphate. Glucose, mannitol, sorbitol or glycerol was used as the source of carbon and energy. Fermentation process parameters followed were that of typical E. coli fermentation process i.e. pH ~6.5 to 7.5, temperature ~25° C. to 42° C. Aeration 0.5 to 2 vvm, etc. Inducer used was IPTG at the concentration ranging from 0.05 mM to 2 mM. Fermentation batch time was ~7 to 8 hours, while cell density achieved was $OD_{(600nm)}$ 60. Growth inhibition was not observed in spite of inducer addition, this helped to achieve higher biomass along with expression of protein of interest. This resulted in higher yield of the process. The expression of modified SAK-protein of interest fusion was 2.5 to 3 g/L and was visible in IB. Depending upon the molar ration of protein of interest and modified SAK in fusion protein, the yield protein of interest will vary.

Example 5

Purification of PTH from the pET21a-Modified SAK-PTH Construct

PTH obtained from example 4, as inclusion bodies were further subjected to isolation and purification steps.

Solubilization of inclusion bodies: The bacterial inclusion bodies of pET21a-modifiedSAK-PTH clone were solubilised in the ratio of 20 ml of solubilization buffer (6M GuHCl, 20 mM Tris-Cl, pH 8.0) per gm of inclusion bodies. Kept with constant stirring at RT for 30-60 minutes.

Refolding: The solubilised inclusion bodies filtered and refolded by fast dilution drop wise into refolding buffer (20 mM Tris-Cl, pH 8.0, 0.5M Arginine, 5% Sorbitol and 1 mM EDTA) at the ratio of 1:20. Refolding was kept at 4-8° C. with constant stirring for 12-14 hours.

Diafiltration: The refolded sample was concentrated to half the volume and then diafiltered against 20 mM Tris-Cl, pH 8.0 (2.5-3 diavolumes). The diafiltered sample was then filtered using 1/0.45 micron filter.

Ek digestion: Digested for 12-14 hrs with enterokinase (Novagen enterokinase) 0.5 units/A 280 of fusion protein at RT in 1 mM $CaCl_2$ to release protein of interest.

Q SEPHAROSE® (Anion Exchange) column: The filtered protein solution was then loaded onto Q-Sepharose column. Equilibration buffer-20 mM Tris-Cl, pH 8.0. Elution buffer-1.0 M NaCl 20 mM Tris-Cl, pH 8.0. Flow rate: 382 cm/h. The flow through was collected. Elution done with a step gradient of 100% B. Column volumes used was 9.0-10.0 ml of resin per gm of inclusion bodies. Volume-250 ml approx for 1 gm inclusion bodies.

SP SEPHAROSE® (Cation Exchange) column: The Q SEPHAROSE® (anion exchange) flow through was adjusted to pH of 6.0 and loaded on to SP-Sepharose column. Equilibration buffer-10 mM Tris-Cl, pH 6.8. Elution buffer-1.0 M NaCl in 10 mM Tris-Cl, pH 6.8. Flow rate: 300 cm/h. Elution done using gradient of 0-15% B in 12.5 CV. Resin volume used was 18.0 ml per gm of Inclusion bodies at a bed height of 9.0 cm. Volume—36 ml per gm of Inclusion bodies.

Hydrophobic Interaction chromatography (Phenyl HP SEPHAROSE®) column: The cation exchange (SP SEPHAROSE®) eluate was adjusted to pH of 4.5 with 1:3 diluted acetic acid and then 1.7 M of ammonium sulphate was added to the protein solution gradually. Equilibration buffer-1.7 M ammonium sulphate in 20 mM Sodium acetate, pH 4.5. Elution buffer: 20 mM Sodium acetate, pH 4.5. Flow rate: 150 cm/h. Elution was done using gradient of 0-50% B in 35 CV. Resin volume used was 9.0 ml per gm of Inclusion bodies at a bed height of 4.5 cm. the eluates were collected and analyzed by RP-HPLC for purity. 50-70 ml per gm inclusion bodies.

Example 6

An Alternate Process for Purification of PTH to Minimize Volume During Refolding Using Urea—A Different Denaturant in Place of Guanidine Hydrochloride Downstream Process Development for PTH from SAK*PTH:

Solubilization and refolding of Inclusion bodies: Solubilisation was carried out using 4 M Urea in 20 mM Tris-Cl, pH 8.0 at room temperature (22° C.-25° C.) for 1-2 hours. Solubilization was followed by centrifugation at 27000 g for 10 minutes at 10-15° C.

EK Digestion: Enterokinase digestion was done using *Pichia* derived human Enterokinase in the range of 16-20 ng per 1 mg of total protein. Digestion was carried out at room temperature (22° C.-25° C.) for 14-20 hours.

Anion Exchange Chromatography (Q SEPHAROSE®) column: The Enterokinase digested protein was filtered using 1.0 micron filter and loaded on to anion exchange using Q-SEPHAROSE® FF (Anion Exchange Column) at pH 8.0 in 20 mM Tris-Cl. Q-SEPHAROSE® FF (Anion Exchange Column) is in the Flow Through mode, i.e., the protein of interest, PTH in this case, comes in the unbound fraction.

Cation Exchange Chromatography: (SP SEPHAROSE®) The pH of the anion exchange (Q SEPHAROSE®) flow thorough was adjusted to pH 4.0 using glacial acetic acid and was then filtered using 1.0 micron filter. The filtrate was then used as the load for Cation exchanger, SP SEPHAROSE® FF (Anion Exchange Column). The buffer used in this step is 20 mM Sodium acetate with and without 1.0 M NaCl. Our protein of interest comes out in the eluate. The conductivity of the above eluate was adjusted to ≥150 mS/cm using sodium chloride as the salt.

Hydrophobic Interaction chromatography: The conductivity adjusted protein in then filtered and used as the load for Hydrophobic Interaction Chromatography (HIC). Phenyl SEPHAROSE® HP (Hydrophobic Interaction chromatography) is used as the HIC resin. Our protein of interest comes out in the eluate.

The above HIC eluate is then readjusted to conductivity ≥150 mS/cm using sodium chloride as the salt and reloaded on Phenyl-Sepharose HP. This second step of HIC is used as a concentration step.

Gel Filtration: Finally the protein of interest is loaded on SEPHADEX® G10 (Gel Filtration Chromatography-GFC) for buffer exchange. The GFC eluate is the final Drug substance which is stored at 2-8° C.

Example 7

Purification of Modified SAK-IL11

IL-11 obtained from example 4 as inclusion bodies was further subjected to isolation and purification steps.

Solubilization of Inclusion bodies: Inclusion bodies were solubilised in the ratio of 20 ml of solubilization buffer (100 mM Tris, 6 M GuCl pH 8.0) per gm of inclusion bodies. Spun at 15000 rpm for 15 minutes. The supernatant was used for refolding.

Refolding: The solubilised inclusion bodies was refolded in two different refolding buffer conditions:

Buffer A: 20 mM Tris, 0.5 M Arginine, 5% Sorbitol, 2 mM EDTA, pH 8.0

Buffer B: 20 mM Tris, 4 M urea, pH 8.0

Diafiltration: The refolded sample was concentrated to half the volume and then diafiltered against 10 mM Tris pH 8.0. The diafiltered sample was then filtered using 1/0.45 micron filter and Spun at 15000 rpm for 15 minutes.

Ek digestion: Digested for 16 hrs with enterokinase (Novagen enterokinase) 2.4 units/0.4 mg of fusion protein at RT in 1 mM $CaCl_2$ to release protein of interest. After digestion the protein sample is spun at 15000 rpm, 15 min and supernatant is used for purification CM SEPHAROSE® column: The filtered protein solution was then loaded onto CM-SEPHAROSE® column. Equilibration buffer-20 mM Tris-Cl, 150 mM glycine, 5 mM Methionine pH 8.0. Elution buffer-125 M NaCl. Eluted protein is >95. % pure on HPLC and SDS-PAGE silver stained gel. The purified protein in WFI was then lyophilized and reconstituted in formulation buffer at the required concentration. The protein is passed through anion exchange column (Q SEPHAROSE®) to remove endotoxins. The CM elution is further loaded onto anion exchange column (Q SEPHAROSE®) at 10-11 ms conductivity in 20 mM Tris pH 8.0 to remove endotoxin, the protein comes in the flow through fraction HPLC profile of Oprelvekin and purified rhIL-11.

The invention claimed is:

1. A fusion DNA comprising a first DNA encoding a modified staphylokinase (SAK) protein comprising the nucleic acid sequence of SEQ ID NO. 1 and a second DNA fused in frame encoding the heterologous protein of interest.

2. The fusion DNA as claimed in claim 1, wherein the second DNA encodes the amino acid sequence as set forth in SEQ ID NO. 2.

3. The fusion DNA as claimed in claim 1, wherein the heterologous protein of interest is selected from the group comprising parathyroid hormone (1-34) as set forth in SEQ ID NO. 4, parathyroid hormone (1-84), reteplase, interferon, IL-2, IL-3, IL-4, IL-5, IL-6, IL-11 as set forth in SEQ ID NO. 6, granulocyte colony stimulating factor (GCSF), epidermal growth factor and platelet derived growth factor.

4. The fusion DNA as claimed in claim 1, wherein the heterologous protein of interest is parathyroid hormone (1-34) encoded by the nucleic acid of SEQ ID NO. 3.

5. The fusion DNA as claimed in claim 1, wherein the heterologous protein of interest is parathyroid hormone (1-34) as set forth in SEQ ID NO. 4.

6. The fusion DNA as claimed in claim 1, wherein the heterologous protein of interest is IL-11 encoded by the nucleic acid of SEQ ID NO. 5.

7. The fusion DNA as claimed in claim 1, wherein the heterologous protein of interest is IL-11 as set forth in SEQ ID NO. 6.

* * * * *

SEQUENCE LISTING

<160> NUMBER OF SEQ ID NOS: 6

<210> SEQ ID NO 1
<211> LENGTH: 441
<212> TYPE: DNA
<213> ORGANISM: Artificial Sequence
<220> FEATURE:
<223> OTHER INFORMATION: Modified SAK

<400> SEQUENCE: 1

| | | |
|---|---|---|
| catatgtcaa gttcattcga caaaggaaaa tataaaaaag gcgatgacgc gagttatttt | 60 | |
| gaaccaacag gcccgtattt gatggtaaat gtgactggag ttgatggtaa aggaaatgag | 120 | |
| ttgctatccc ctcattatgt cgagtttcct attaaacctg gactacact tacaaaagaa | 180 | |
| aaaattgaat acgatgatga tgataaagaa tgggcattag atgcgacagc atataaagag | 240 | |
| tttagagtag ttgaattaga tccaagcgca aagatcgaag tcacttatta tgataagaat | 300 | |
| aagaaaaaag aagaaacgaa gtctttccct ataacgaaa aaggttttgt tgtcccagat | 360 | |
| ttatcagagc atattaaaaa ccctggattc aacttaatta caaggttgt tatagaaaag | 420 | |
| aaagatgatg atgataaata a | 441 | |

<210> SEQ ID NO 2
<211> LENGTH: 151
<212> TYPE: PRT
<213> ORGANISM: Artificial Sequence
<220> FEATURE:
<223> OTHER INFORMATION: Modified SAK

<400> SEQUENCE: 2

Met Ser Ser Ser Phe Asp Lys Gly Lys Tyr Lys Lys Gly Asp Asp Ala
1               5                   10                  15

Ser Tyr Phe Glu Pro Thr Gly Pro Tyr Leu Met Val Asn Val Thr Gly
            20                  25                  30

Val Asp Gly Lys Gly Asn Glu Leu Leu Ser Pro His Tyr Val Glu Phe
        35                  40                  45

Pro Ile Lys Pro Gly Thr Thr Leu Thr Lys Glu Lys Ile Glu Tyr Leu
    50                  55                  60

Gln Asp Asp Asp Lys Tyr Val Glu Trp Ala Leu Asp Ala Thr Ala
65                  70                  75                  80

Tyr Lys Glu Phe Arg Val Val Glu Leu Asp Pro Ser Ala Lys Ile Glu
                85                  90                  95

Val Thr Tyr Tyr Asp Lys Asn Lys Lys Glu Glu Thr Lys Ser Phe
            100                 105                 110

Pro Ile Thr Glu Lys Gly Phe Val Val Pro Asp Leu Ser Glu His Ile
        115                 120                 125

Lys Asn Pro Gly Phe Asn Leu Ile Thr Lys Val Val Ile Glu Lys Lys
    130                 135                 140

Gly Ser Asp Asp Asp Asp Lys
145                 150

<210> SEQ ID NO 3
<211> LENGTH: 561
<212> TYPE: DNA
<213> ORGANISM: Artificial Sequence
<220> FEATURE:
<223> OTHER INFORMATION: Modified SAK-PTH fusion protein

<400> SEQUENCE: 3
catatgtcaa gttcattcga caaaggaaaa tataaaaaag gcgatgacgc gagttatttt    60

```
gaaccaacag gcccgtattt gatggtaaat gtgactggag ttgatggtaa aggaaatgag    120
ttgctatccc ctcattatgt cgagtttcct attaaacctg ggactacact tacaaaagaa    180
aaaattgaat acctgcagga tgatgatgat aaatacgtag aatgggcatt agatgcgaca    240
gcatataaag agtttagagt agttgaatta gatccaagcg caaagatcga agtcacttat    300
tatgataaga ataagaaaaa agaagaaacg aagtcttttc ctataacaga aaaaggtttt    360
gttgtcccag atttatcaga gcatattaaa aaccctggat caacttaat tacaaaggtt    420 gttatagaaa agaaaggatc cgatgatgat gataaatctg tgtccgagat tcagttaatg    480
cataaccttg gcaaacattt gaactccatg gagcgtgtag aatggctgcg taagaagttg    540
caggatgtgc acaatttta a                                               561

<210> SEQ ID NO 4
<211> LENGTH: 185
<212> TYPE: PRT
<213> ORGANISM: Artificial Sequence
<220> FEATURE:
<223> OTHER INFORMATION: Modified SAK-PTH fusion protein

<400> SEQUENCE: 4

Met Ser Ser Ser Phe Asp Lys Gly Lys Tyr Lys Lys Gly Asp Asp Ala
1               5                   10                  15

Ser Tyr Phe Glu Pro Thr Gly Pro Tyr Leu Met Val Asn Val Thr Gly
            20                  25                  30

Val Asp Gly Lys Gly Asn Glu Leu Leu Ser Pro His Tyr Val Glu Phe
        35                  40                  45

Pro Ile Lys Pro Gly Thr Thr Leu Thr Lys Glu Lys Ile Glu Tyr Leu
    50                  55                  60

Gln Asp Asp Asp Lys Tyr Val Glu Trp Ala Leu Asp Ala Thr Ala
65                  70                  75                  80

Tyr Lys Glu Phe Arg Val Val Glu Leu Asp Pro Ser Ala Lys Ile Glu
                85                  90                  95

Val Thr Tyr Tyr Asp Lys Asn Lys Lys Glu Glu Thr Lys Ser Phe
            100                 105                 110

Pro Ile Thr Glu Lys Gly Phe Val Val Pro Asp Leu Ser Glu His Ile
        115                 120                 125

Lys Asn Pro Gly Phe Asn Leu Ile Thr Lys Val Ile Glu Lys Lys
    130                 135                 140

Gly Ser Asp Asp Asp Lys Ser Val Ser Glu Ile Gln Leu Met His
145                 150                 155                 160

Asn Leu Gly Lys His Leu Asn Ser Met Glu Arg Val Glu Trp Leu Arg
                165                 170                 175

Lys Lys Leu Gln Asp Val His Asn Phe
            180                 185

<210> SEQ ID NO 5
<211> LENGTH: 990
<212> TYPE: DNA
<213> ORGANISM: Artificial Sequence
<220> FEATURE:
<223> OTHER INFORMATION: Modified SAK-IL-11 fusion protein

<400> SEQUENCE: 5
catatgtcaa gttcattcga caaaggaaaa tataaaaaag cgatgacgc gagttatttt     60 gaaccaacag gcccgtattt gatggtaaat gtgactggag ttgatggtaa aggaaatgag    120
```

```
ttgctatccc ctcattatgt cgagtttcct attaaacctg ggactacact tacaaaagaa    180
aaaattgaat acctgcagga tgatgatgat aaatacgtag aatgggcatt agatgcgaca    240
gcatataaag agtttagagt agttgaatta gatccaagcg caaagatcga agtcacttat    300
tatgataaga ataagaaaaa agaagaaacg aagtcttttcc ctataacaga aaaaggtttt    360
```

```
ttgctatccc ctcattatgt cgagtttcct attaaacctg ggactacact tacaaaagaa    180
aaaattgaat acctgcagga tgatgatgat aaatacgtag aatgggcatt agatgcgaca    240
gcatataaag agtttagagt agttgaatta gatccaagcg caaagatcga agtcacttat    300
tatgataaga ataagaaaaa agaagaaacg aagtcttttcc ctataacaga aaaaggtttt    360
gttgtcccag atttatcaga gcatattaaa aaccctggat tcaacttaat tacaaaggtt    420
gttatagaaa agaaaggatc cgatgatgat gataaagggc caccacctgg cccccctcga    480
gtttccccag accctcgggc cgagctggac agcaccgtgc tcctgacccg ctctctcctg    540
gcggacacgc ggcagctggc tgcacagctg agggacaaat ccccagctga cggggaccac    600
aacctggatt ccctgcccac cctggccatg agtgcggggg cactgggagc tctacagctc    660
ccaggtgtgc tgacaaggct gcgagcggac ctactgtcct acctgcggca cgtgcagtgg    720
ctgcgccggg caggtggctc ttccctgaag accctggagc cgagctggg caccctgcag    780 gcccgactgg accggctgct cgcgcggctg cagctcctga tgtcccgcct ggccctgccc    840
cagccacccc cggacccgcc ggcgccccg ctggcgcccc cctcctcagc ctgggggggc    900
atcagggccg cccacgccat cctggggggg ctgcacctga cacttgactg ggccgtgagg    960
ggactgctgc tgctgaagac tcggctgtga                                    990
```

<210> SEQ ID NO 6
<211> LENGTH: 328
<212> TYPE: PRT
<213> ORGANISM: Artificial Sequence
<220> FEATURE:
<223> OTHER INFORMATION: Modified SAK-IL-11 fusion protein

<400> SEQUENCE: 6

```
Met Ser Ser Ser Phe Asp Lys Gly Lys Tyr Lys Lys Gly Asp Asp Ala
1               5                   10                  15

Ser Tyr Phe Glu Pro Thr Gly Pro Tyr Leu Met Val Asn Val Thr Gly
            20                  25                  30

Val Asp Gly Lys Gly Asn Glu Leu Leu Ser Pro His Tyr Val Glu Phe
        35                  40                  45

Pro Ile Lys Pro Gly Thr Thr Leu Thr Lys Glu Lys Ile Glu Tyr Leu
    50                  55                  60

Gln Asp Asp Asp Lys Tyr Val Glu Trp Ala Leu Asp Ala Thr Ala
65                  70                  75                  80

Tyr Lys Glu Phe Arg Val Val Glu Leu Asp Pro Ser Ala Lys Ile Glu
                85                  90                  95

Val Thr Tyr Tyr Asp Lys Asn Lys Lys Glu Thr Lys Ser Phe
            100                 105                 110

Pro Ile Thr Glu Lys Gly Phe Val Val Pro Asp Leu Ser Glu His Ile
        115                 120                 125

Lys Asn Pro Gly Phe Asn Leu Ile Thr Lys Val Val Ile Glu Lys Lys
    130                 135                 140

Gly Ser Asp Asp Asp Lys Gly Pro Pro Gly Pro Pro Arg Val
145                 150                 155                 160

Ser Pro Asp Pro Arg Ala Glu Leu Asp Ser Thr Val Leu Leu Thr Arg
                165                 170                 175

Ser Leu Leu Ala Asp Thr Arg Gln Leu Ala Ala Gln Leu Arg Asp Lys
            180                 185                 190

Phe Pro Ala Asp Gly Asp His Asn Leu Asp Ser Leu Pro Thr Leu Ala
        195                 200                 205
```

```
Met Ser Ala Gly Ala Leu Gly Ala Leu Gln Leu Pro Gly Val Leu Thr
    210                 215                 220

Arg Leu Arg Ala Asp Leu Leu Ser Tyr Leu Arg His Val Gln Trp Leu
225             230                 235                 240

Arg Arg Ala Gly Gly Ser Ser Leu Lys Thr Leu Glu Pro Glu Leu Gly
            245                 250                 255

Thr Leu Gln Ala Arg Leu Asp Arg Leu Leu Arg Arg Leu Gln Leu Leu
            260                 265                 270

Met Ser Arg Leu Ala Leu Pro Gln Pro Pro Pro Asp Pro Pro Ala Pro
        275                 280                 285

Pro Leu Ala Pro Pro Ser Ser Ala Trp Gly Gly Ile Arg Ala Ala His
    290                 295                 300

Ala Ile Leu Gly Gly Leu His Leu Thr Leu Asp Trp Ala Val Arg Gly
305                 310                 315                 320

Leu Leu Leu Leu Lys Thr Arg Leu
                325
```